United States Patent
Shankar Setty et al.

(10) Patent No.: US 10,993,714 B2
(45) Date of Patent: May 4, 2021

(54) SURGICAL STAPLING INSTRUMENT AND ASSOCIATED TRIGGER MECHANISMS

(71) Applicant: Covidien LP, Mansfield, MA (US)

(72) Inventors: Jeevan Maddur Shankar Setty, Bangalore (IN); Sabastian Koduthully George, Hyderabad (IN); Syed Sarfraz Ahamed, Bangalore (IN); Anant Tiwari, Madhya Pradesh (IN)

(73) Assignee: Covidien LP, Mansfield, MA (US)

( * ) Notice: Subject to any disclaimer, the term of this patent is extended or adjusted under 35 U.S.C. 154(b) by 256 days.

(21) Appl. No.: 16/179,039

(22) Filed: Nov. 2, 2018

(65) Prior Publication Data

US 2019/0159775 A1 May 30, 2019

Related U.S. Application Data

(60) Provisional application No. 62/591,735, filed on Nov. 28, 2017.

(51) Int. Cl.
*A61B 17/072* (2006.01)
*A61B 17/00* (2006.01)
*A61B 17/29* (2006.01)

(52) U.S. Cl.
CPC .. *A61B 17/072* (2013.01); *A61B 2017/00367* (2013.01); *A61B 2017/00477* (2013.01); *A61B 2017/07257* (2013.01); *A61B 2017/07271* (2013.01); *A61B 2017/07285* (2013.01); *A61B 2017/2922* (2013.01); *A61B 2017/2925* (2013.01)

(58) Field of Classification Search
CPC ........ A61B 17/072; A61B 2017/00367; A61B 2017/00477; A61B 2017/07257; A61B 2017/07271; A61B 2017/07285; A61B 2017/2922; A61B 2017/2925
USPC .............. 227/175.1–182.1; 606/75, 219, 220
See application file for complete search history.

(56) References Cited

U.S. PATENT DOCUMENTS

| | | |
|---|---|---|
| 1,158,111 A | 10/1915 | Ahlheim |
| 2,891,250 A | 6/1959 | Hirata |
| 3,080,564 A | 3/1963 | Strekopitov et al. |
| 3,252,643 A | 5/1966 | Strekopov et al. |
| 3,269,630 A | 8/1966 | Fleischer |
| 3,275,211 A | 9/1966 | Hirsch et al. |
| 3,315,863 A | 4/1967 | O'Dea |

(Continued)

FOREIGN PATENT DOCUMENTS

EP 2033585 A1 3/2009

OTHER PUBLICATIONS

European Search Report dated Apr. 17, 2019, issued in EP Appln. No. 18208642.

(Continued)

*Primary Examiner* — Dariush Seif
(74) *Attorney, Agent, or Firm* — Carter, DeLuca & Farrell LLP (57) ABSTRACT

A trigger mechanism for a surgical instrument, particularly, a surgical stapling instrument provides significant mechanical advantages by increasing the length of the firing stroke of the surgical instrument while reducing the degree of movement of the trigger associated with the trigger mechanism. The trigger mechanism also reduces the forces required to actuate the trigger thereby enhancing usability and minimizing operator fatigue.

4 Claims, 8 Drawing Sheets

(56) References Cited

U.S. PATENT DOCUMENTS

| | | | |
|---|---|---|---|
| 3,494,533 | A | 2/1970 | Green et al. |
| 3,589,589 | A | 6/1971 | Akopov |
| 3,692,224 | A | 9/1972 | Astafiev et al. |
| 3,795,034 | A | 3/1974 | Strekopytov et al. |
| 3,822,818 | A | 7/1974 | Strekopytov et al. |
| 3,935,981 | A | 2/1976 | Akopov et al. |
| 3,949,923 | A | 4/1976 | Akopov et al. |
| 3,955,581 | A * | 5/1976 | Spasiano .............. A61B 17/068 227/175.1 |
| 4,047,654 | A | 9/1977 | Alvarado |
| 4,216,891 | A | 8/1980 | Behlke |
| 4,244,372 | A | 1/1981 | Kapitanov et al. |
| 4,296,881 | A | 10/1981 | Lee |
| 4,305,539 | A | 12/1981 | Korolkov et al. |
| 4,354,628 | A | 10/1982 | Green |
| 4,378,901 | A | 4/1983 | Akopov et al. |
| 4,383,634 | A | 5/1983 | Green |
| 4,402,444 | A | 9/1983 | Green |
| 4,415,112 | A | 11/1983 | Green |
| D273,513 | S | 4/1984 | Spreckelmeier |
| 4,442,964 | A | 4/1984 | Becht |
| 4,470,533 | A | 9/1984 | Schuler |
| 4,475,679 | A | 10/1984 | Fleury, Jr. |
| 4,485,811 | A | 12/1984 | Chernousov et al. |
| 4,506,670 | A | 3/1985 | Crossley |
| 4,506,671 | A | 3/1985 | Green |
| 4,508,253 | A | 4/1985 | Green |
| 4,522,327 | A | 6/1985 | Korthoff et al. |
| 4,527,724 | A | 7/1985 | Chow et al. |
| 4,530,453 | A | 7/1985 | Green |
| 4,550,870 | A | 11/1985 | Krumme et al. |
| 4,566,620 | A | 1/1986 | Green et al. |
| 4,568,009 | A | 2/1986 | Green |
| 4,573,622 | A | 3/1986 | Green et al. |
| 4,580,712 | A | 4/1986 | Green |
| 4,585,153 | A | 4/1986 | Failla et al. |
| 4,589,582 | A | 5/1986 | Bilotti |
| 4,602,634 | A | 7/1986 | Barkley |
| 4,605,001 | A | 8/1986 | Rothfuss et al. |
| 4,605,004 | A * | 8/1986 | Di Giovanni ........ A61B 17/072 112/169 |
| 4,606,344 | A | 8/1986 | Di Giovanni |
| 4,606,345 | A | 8/1986 | Dorband et al. |
| 4,607,636 | A | 8/1986 | Kula et al. |
| 4,612,933 | A | 9/1986 | Brinkerhoff et al. |
| 4,617,928 | A | 10/1986 | Alfranca |
| 4,632,290 | A | 12/1986 | Green et al. |
| 4,665,916 | A | 5/1987 | Green |
| 4,684,051 | A | 8/1987 | Akopov et al. |
| 4,714,187 | A | 12/1987 | Green |
| 4,715,520 | A | 12/1987 | Roehr, Jr. et al. |
| 4,728,020 | A | 3/1988 | Green et al. |
| 4,767,044 | A | 8/1988 | Green |
| 4,788,978 | A | 12/1988 | Strekopytov et al. |
| 4,802,614 | A | 2/1989 | Green et al. |
| 4,805,823 | A | 2/1989 | Rothfuss |
| 4,819,853 | A | 4/1989 | Green |
| 4,848,637 | A | 7/1989 | Pruitt |
| 4,869,414 | A | 9/1989 | Green et al. |
| 4,881,544 | A | 11/1989 | Green et al. |
| 4,881,545 | A | 11/1989 | Isaacs et al. |
| 4,915,100 | A | 4/1990 | Green |
| 4,930,503 | A | 6/1990 | Pruitt |
| 4,938,408 | A | 7/1990 | Bedi et al. |
| 4,941,623 | A | 7/1990 | Pruitt |
| 4,951,861 | A | 8/1990 | Schulze et al. |
| 4,964,559 | A | 10/1990 | Deniega et al. |
| 5,005,754 | A | 4/1991 | Van Overloop |
| 5,018,657 | A | 5/1991 | Pedlick et al. |
| 5,071,052 | A * | 12/1991 | Rodak .................. A61B 17/072 227/175.2 |
| 5,100,042 | A | 3/1992 | Gravener et al. |
| 5,116,349 | A | 5/1992 | Aranyi |
| 5,137,198 | A * | 8/1992 | Nobis .................. A61B 17/072 227/175.3 |
| 5,172,845 | A | 12/1992 | Tejeiro |
| 5,190,203 | A * | 3/1993 | Rodak .................. A61B 17/072 227/175.1 |
| 5,219,111 | A | 6/1993 | Bilotti et al. |
| 5,240,163 | A * | 8/1993 | Stein .................... A61B 17/072 227/175.3 |
| 5,258,010 | A * | 11/1993 | Green ................ A61B 17/0682 227/176.1 |
| 5,344,060 | A | 9/1994 | Gravener et al. |
| 5,368,599 | A | 11/1994 | Hirsch et al. |
| 5,405,073 | A | 4/1995 | Porter |
| 5,413,267 | A | 5/1995 | Solyntjes et al. |
| 5,439,155 | A | 8/1995 | Viola |
| 5,452,836 | A * | 9/1995 | Huitema .............. A61B 17/072 227/176.1 |
| 5,458,279 | A | 10/1995 | Plyley |
| 5,462,215 | A | 10/1995 | Viola et al. |
| 5,464,144 | A | 11/1995 | Guy et al. |
| 5,465,894 | A | 11/1995 | Clark et al. |
| 5,470,006 | A | 11/1995 | Rodak |
| 5,470,008 | A | 11/1995 | Rodak |
| 5,470,009 | A | 11/1995 | Rodak |
| 5,497,934 | A | 3/1996 | Brady et al. |
| 5,503,320 | A | 4/1996 | Webster et al. |
| 5,509,596 | A * | 4/1996 | Green .................. A61B 17/072 227/176.1 |
| 5,542,594 | A | 8/1996 | McKean et al. |
| 5,547,117 | A * | 8/1996 | Hamblin .............. A61B 17/072 227/175.2 |
| 5,558,266 | A | 9/1996 | Green et al. |
| 5,579,978 | A | 12/1996 | Green et al. |
| 5,580,067 | A | 12/1996 | Hamblin et al. |
| 5,603,443 | A | 2/1997 | Clark et al. |
| 5,605,272 | A * | 2/1997 | Witt ...................... A61B 17/072 227/175.2 |
| 5,605,273 | A | 2/1997 | Hamblin et al. |
| 5,607,094 | A | 3/1997 | Clark et al. |
| 5,615,820 | A | 4/1997 | Viola |
| 5,641,111 | A | 6/1997 | Ahrens et al. |
| 5,678,748 | A | 10/1997 | Plyley et al. |
| 5,697,543 | A | 12/1997 | Burdorff |
| 5,706,997 | A | 1/1998 | Green et al. |
| 5,706,998 | A | 1/1998 | Plyley et al. |
| 5,732,871 | A | 3/1998 | Clark et al. |
| 5,735,445 | A | 4/1998 | Vidal et al. |
| 5,794,834 | A | 8/1998 | Hamblin et al. |
| 5,810,240 | A | 9/1998 | Robertson |
| 5,855,311 | A | 1/1999 | Hamblin et al. |
| 5,878,937 | A | 3/1999 | Green et al. |
| 5,893,506 | A | 4/1999 | Powell |
| 5,894,979 | A | 4/1999 | Powell |
| 5,964,394 | A | 10/1999 | Robertson |
| 6,045,560 | A | 4/2000 | McKean et al. |
| 6,079,606 | A * | 6/2000 | Milliman ......... A61B 17/07207 227/175.2 |
| 6,638,285 | B2 | 10/2003 | Gabbay |
| 6,805,273 | B2 | 10/2004 | Bilotti et al. |
| 6,817,508 | B1 | 11/2004 | Racenet et al. |
| 6,988,650 | B2 | 1/2006 | Schwemberger et al. |
| 7,070,083 | B2 | 7/2006 | Jankowski |
| 7,134,587 | B2 | 11/2006 | Schwemberger et al. |
| 7,147,139 | B2 | 12/2006 | Schwemberger et al. |
| 7,147,140 | B2 | 12/2006 | Wukusick et al. |
| 7,204,404 | B2 | 4/2007 | Nguyen et al. |
| 7,207,472 | B2 | 4/2007 | Wukusick et al. |
| 7,210,609 | B2 | 5/2007 | Leiboff et al. |
| 7,237,708 | B1 | 7/2007 | Guy et al. |
| 7,275,674 | B2 | 10/2007 | Racenet et al. |
| RE40,237 | E | 4/2008 | Bilotti et al. |
| 7,407,076 | B2 | 8/2008 | Racenet et al. |
| 7,431,190 | B2 | 10/2008 | Hoffman |
| 7,441,685 | B1 * | 10/2008 | Boudreaux ...... A61B 17/07207 227/176.1 |
| 7,522,854 | B2 | 4/2009 | Kinouchi et al. |
| 7,549,563 | B2 | 6/2009 | Mather et al. |
| 7,568,605 | B2 | 8/2009 | Kruszynski |
| 7,641,092 | B2 | 1/2010 | Kruszynski et al. |
| 7,717,312 | B2 | 5/2010 | Beetel |

(56) References Cited

U.S. PATENT DOCUMENTS

| | | |
|---|---|---|
| 7,731,073 B2 | 6/2010 | Wixey et al. |
| 7,735,704 B2 | 6/2010 | Bilotti |
| 7,766,207 B2 | 8/2010 | Mather et al. |
| 7,810,690 B2 | 10/2010 | Bilotti et al. |
| 7,886,953 B2 | 2/2011 | Schwemberger et al. |
| 8,016,176 B2 | 9/2011 | Kasvikis et al. |
| 8,029,520 B2 | 10/2011 | Korvick et al. |
| 8,033,439 B2 | 10/2011 | Racenet et al. |
| 8,070,038 B2 | 12/2011 | Kostrzewski |
| 8,231,041 B2 | 7/2012 | Marczyk et al. |
| 8,292,904 B2 | 10/2012 | Popovic et al. |
| 8,360,296 B2 | 1/2013 | Zingman |
| 8,424,738 B2 | 4/2013 | Kasvikis |
| 8,499,994 B2 | 8/2013 | D'Arcangelo |
| 8,596,515 B2 | 12/2013 | Okoniewski |
| 8,627,994 B2 | 1/2014 | Zemlok et al. |
| 8,646,673 B2 | 2/2014 | Bilotti et al. |
| 8,757,467 B2 | 6/2014 | Racenet et al. |
| 8,936,185 B2 | 1/2015 | Racenet et al. |
| 8,955,732 B2 | 2/2015 | Zemlok et al. |
| 8,967,446 B2 | 3/2015 | Beardsley et al. |
| 9,022,273 B1 | 5/2015 | Marczyk et al. |
| 9,125,651 B2 | 9/2015 | Mandakolathur Vasudevan et al. |
| 9,192,382 B2 | 11/2015 | Kostrzewski |
| 10,864,005 B2 * | 12/2020 | Windgassen ....... A61B 17/2909 |
| 2004/0164123 A1 * | 8/2004 | Racenet ............... A61B 17/072 227/176.1 |
| 2005/0247752 A1 | 11/2005 | Kelly et al. |
| 2005/0247753 A1 | 11/2005 | Kelly et al. |
| 2005/0263563 A1 * | 12/2005 | Racenet ............... A61B 17/072 227/176.1 |
| 2006/0163312 A1 | 7/2006 | Viola et al. |
| 2007/0095877 A1 * | 5/2007 | Racenet ............... A61B 17/072 227/175.2 |
| 2007/0187456 A1 | 8/2007 | Viola et al. |
| 2010/0048988 A1 | 2/2010 | Pastorelli et al. |
| 2013/0206813 A1 | 8/2013 | Nalagatla |
| 2014/0191013 A1 * | 7/2014 | Natarajan ............ A61B 17/068 227/176.1 |
| 2014/0263555 A1 * | 9/2014 | Hufnagel ......... A61B 17/00234 227/176.1 |
| 2016/0249914 A1 | 9/2016 | Zhang et al. |
| 2017/0014134 A1 | 1/2017 | Chen et al. |
| 2017/0027571 A1 | 2/2017 | Nalagatla et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |
| 2020/0046328 A1 * | 2/2020 | Zammataro ............ A61B 17/00 |
| 2020/0261095 A1 * | 8/2020 | Yi ...................... A61B 17/1285 |
| 2020/0337698 A1 * | 10/2020 | Simms ................ A61B 17/072 |
| 2020/0337699 A1 * | 10/2020 | Rector ................ A61B 17/072 |
| 2020/0337700 A1 * | 10/2020 | Hontz .............. A61B 17/07207 |

OTHER PUBLICATIONS

Extended European Search Report for Application No. 18208642.1 dated Oct. 6, 2020.

* cited by examiner

SURGICAL STAPLING INSTRUMENT AND ASSOCIATED TRIGGER MECHANISMS

CROSS-REFERENCE TO RELATED APPLICATIONS

This application claims the benefit of and priority to U.S. Provisional Patent Application No. 62/591,735, filed Nov. 28, 2017, the entire disclosure of which is incorporated by reference herein.

BACKGROUND

1. Technical Field

The present disclosure generally relates to a surgical instrument and, more particularly, relates to a trigger mechanism for use with a stapling instrument and adapted to enhance the mechanical advantage and reduce the firing forces required to actuate the stapling instrument.

2. Background of Related Art

Stapling instruments for applying staples through compressed living tissue are commonly used, e.g., for closure of tissue or organs prior to transection, prior to resection, or in an anastomoses, and/or for the occlusion of organs in thoracic and abdominal procedures. In general, stapling instruments include an anvil assembly, a cartridge assembly for supporting an array of surgical staples, an approximation mechanism for approximating the anvil and cartridge assemblies, and a firing mechanism for ejecting the surgical staples from the cartridge assembly. The approximation mechanism and the firing mechanism may or may not include distinct actuators for effecting approximation and firing of the staples.

Typically, stapling instruments, particularly, mechanically actuated or non-motorized stapling instruments, require the operator to manipulate the actuators with a single hand. However, the forces required to approximate the anvil and cartridge assemblies and/or fire the firing mechanism are relatively substantial in these mechanical systems, which may present difficulties to the operator or cause operator fatigue.

SUMMARY

Accordingly, the present disclosure is directed to improvements in mechanically actuated trigger mechanisms for surgical instruments, particularly, surgical stapling instruments. In one exemplary embodiment, a surgical instrument includes a handle having a handle frame defining a longitudinal handle axis, an elongate member extending from the handle frame, an end effector coupled to the elongate member, a thrust member extending through the elongate member and coupled to the end effector and being configured for longitudinal movement to control operation of the end effector, and a trigger mechanism. The trigger mechanism includes a trigger pivotally mounted to the handle frame and configured for movement between an initial position and an actuated position and a thrust link coupled to the trigger and operatively engageable with the thrust member. The thrust link extends at a fixed link angle relative to the longitudinal axis and is longitudinally advanceable while maintaining the fixed link angle upon movement of the trigger from the initial position to the actuated position to cause corresponding advancing movement of the thrust member and operation of the end effector. In embodiments, the fixed link angle ranges from 1° to 30°.

In another exemplary embodiment, a surgical instrument includes a handle having a handle frame defining a longitudinal handle axis, an elongate member extending from the handle frame, an end effector coupled to the elongate member, a thrust member extending through the elongate member and coupled to the end effector and being configured for longitudinal movement to control operation of the end effector, and a trigger mechanism. The trigger mechanism includes a trigger pivotally mounted to the handle frame and configured for movement between an initial position and an actuated position and a thrust link coupled to the trigger and operatively engageable with the thrust member. The thrust link defines an elongated slot for reception of a thrust link pin which is mounted to the trigger. The thrust link is configured to pivot about the thrust link pin and to longitudinally advance upon movement of the trigger from the initial position to the actuated position to cause corresponding advancing movement of the thrust member and operation of the end effector.

In embodiments, the elongated slot of the thrust link defines a proximal end and a distal end. The thrust link is positioned adjacent the distal end of the elongated slot when in the initial position of the trigger and configured to traverse the elongated slot for positioning adjacent the proximal end of the elongated slot upon movement of the trigger to the actuated position.

In another exemplary embodiment, a surgical instrument includes a handle having a handle frame defining a longitudinal handle axis and an internal guide member with an internal guide surface, an elongate member extending from the handle frame, an end effector coupled to the elongate member, a thrust member extending through the elongate member and coupled to the end effector and configured for longitudinal movement to control operation of the end effector, and a trigger mechanism. The trigger mechanism includes a trigger pivotally mounted to the handle frame and configured for movement between an initial position and an actuated position and a thrust link coupled to the trigger. The thrust link has a forward drive cam engageable with a thrust bar arm of the thrust member and a guide cam engageable with the internal guide surface of the guide member of the handle frame. The thrust link is configured to pivot upon movement of the trigger from the initial position to the actuated position through traversing movement of the guide cam along the internal guide surface of the guide member to cause corresponding traversing movement of the forward drive cam of the thrust link along the thrust bar arm of the thrust member to cause advancing movement of the thrust member through at least a first stage of longitudinal movement to operate the end effector.

In embodiments, the internal guide surface of the internal guide member is arranged in oblique relation to the longitudinal handle axis. In some embodiments, the trigger is operable between the initial position, the actuated position and a partial actuated position intermediate the initial and actuated positions. In certain embodiments, the guide member of the handle frame is configured such that the internal guide surface is released relative to the guide cam of the thrust link upon movement of the trigger beyond the partial actuated position whereby continued movement of the trigger to the actuated position drives the thrust link in a linear manner.

The trigger mechanisms described herein provide mechanical advantages by increasing the length of the firing stroke of the surgical instrument while reducing the degree of movement of the trigger associated with the trigger mechanism. The trigger mechanism also reduces the forces required to actuate the trigger thereby enhancing usability and minimizing operator fatigue.

Other features of the present disclosure will be appreciated from the following description.

BRIEF DESCRIPTION OF THE DRAWINGS

Various embodiments of the presently disclosed trigger mechanisms for use with a surgical instrument are described herein below with reference to the drawings, wherein.

DETAILED DESCRIPTION OF EMBODIMENTS

The presently disclosed trigger mechanisms for use with a surgical instrument will now be described in detail with reference to the drawings in which like reference numerals designate identical or corresponding elements in each of the several views. In this description, the term "proximal" is used generally to refer to that portion of the instrument that is closer to a clinician, while the term "distal" is used generally to refer to that portion of the instrument that is farther from the clinician. In addition, the term clinician is used generally to refer to medical personnel including doctors, nurses, and support personnel.

The exemplary surgical instrument is a stapling instrument including a handle, an elongate member, and an end effector coupled to the elongate member. The end effector may include a staple cartridge and an anvil. At least one manually actuated trigger is mounted to the handle and is adapted to approximate the staple cartridge and the anvil to clamp tissue therebetween and to actuate the firing mechanism to deliver the staples through the tissue for crimping against the anvil and/or deliver a knife to sever tissue between the applied staples. The trigger is coupled to a linkage system which reduces the forces required to fire the staples and advance the knife.

Although the following discussion will focus on the use of the trigger mechanism in connection with a surgical stapling instrument, the trigger mechanism may be utilized in any instrument where a trigger is mechanically actuated to drive a drive member to control operation of an end effector. Examples of such instruments include biopsy instruments, forceps, graspers, etc.

Figure 1:
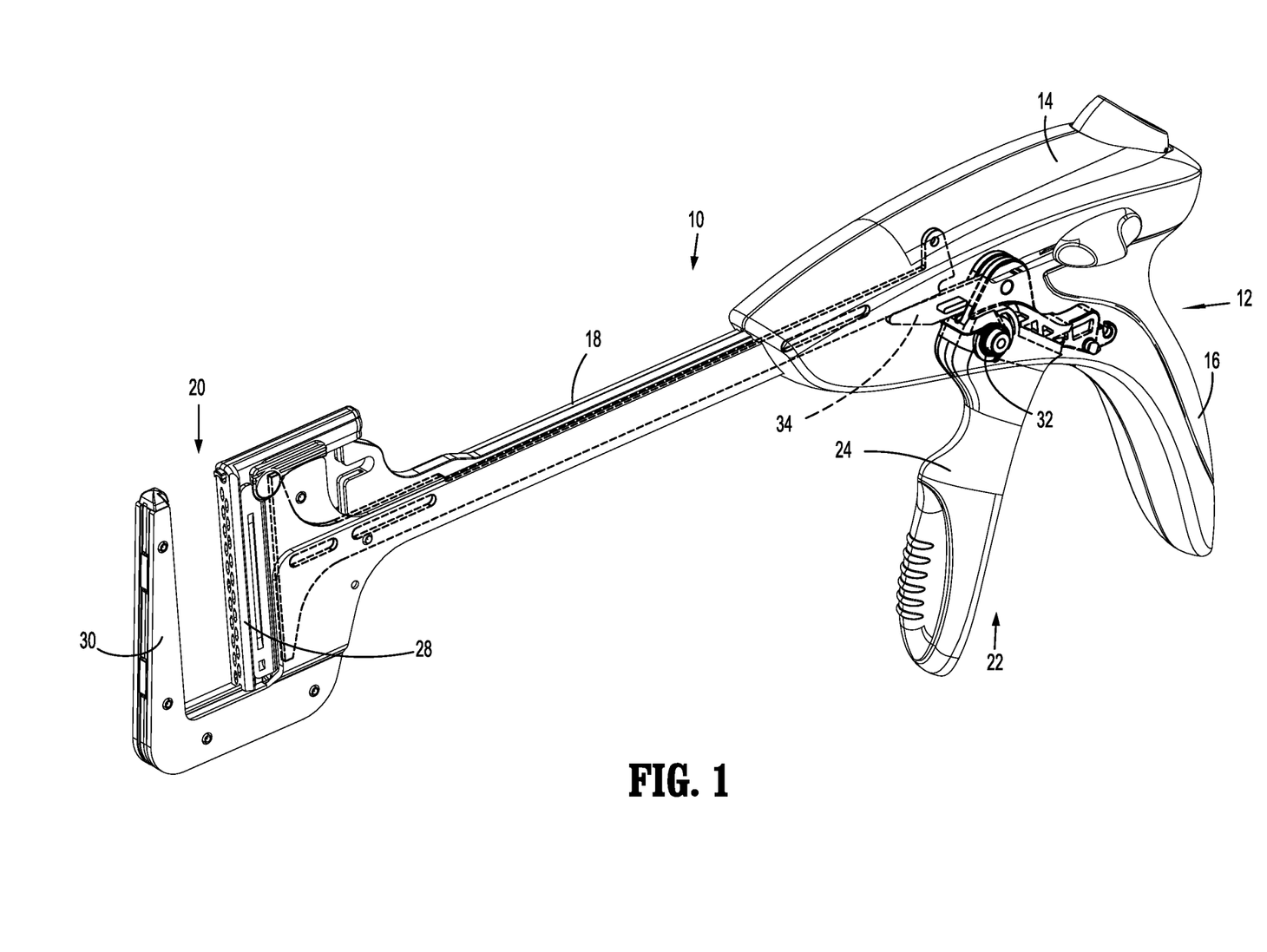
FIG. 1 is a perspective view of a surgical stapling instrument with a trigger mechanism in accordance with one exemplary embodiment of the present disclosure.
Figure 2:
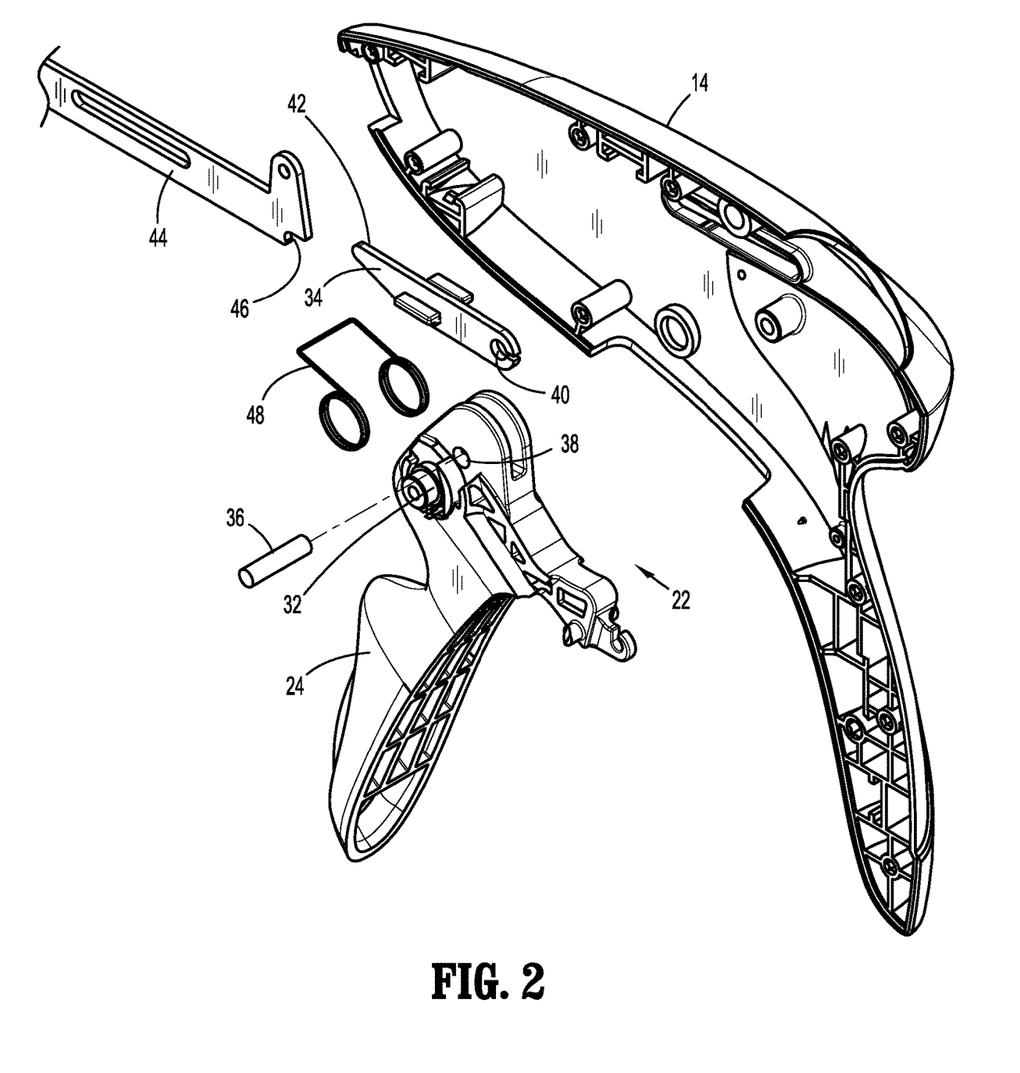
FIG. 2 is an exploded perspective view of the handle of the stapling instrument.

Referring to FIGS. 1-2, the stapling instrument incorporating the trigger mechanism of the present disclosure is illustrated and shown generally as stapling instrument 10. The stapling instrument 10 includes a handle 12 having a handle frame 14 defining a grip 16, an elongate member 18 extending from the handle frame 14, and an end effector 20 coupled to the elongate member 18. A trigger mechanism 22 including a trigger 24 is mounted to the handle frame 14 and is adapted to pivot between initial and actuated positions to control operation of the end effector 20. The end effector 20 includes a staple cartridge 28 housing a plurality of staples (not shown) and an anvil 30 for crimping the staples ejected from the staple cartridge 28. The stapling instrument 10 shares common features with the stapling instrument disclosed in commonly assigned U.S. Pat. No. 6,817,508, the entire contents of which are incorporated by reference herein.

In the following description, only the functioning of the trigger mechanism to drive the staples from the staple cartridge 28 of the end effector 20 will be discussed. Details of the approximation mechanism for approximating the staple cartridge 28 and the anvil 30 may be ascertained by reference to the aforementioned U.S. Pat. No. 6,817,508.

Figure 3:
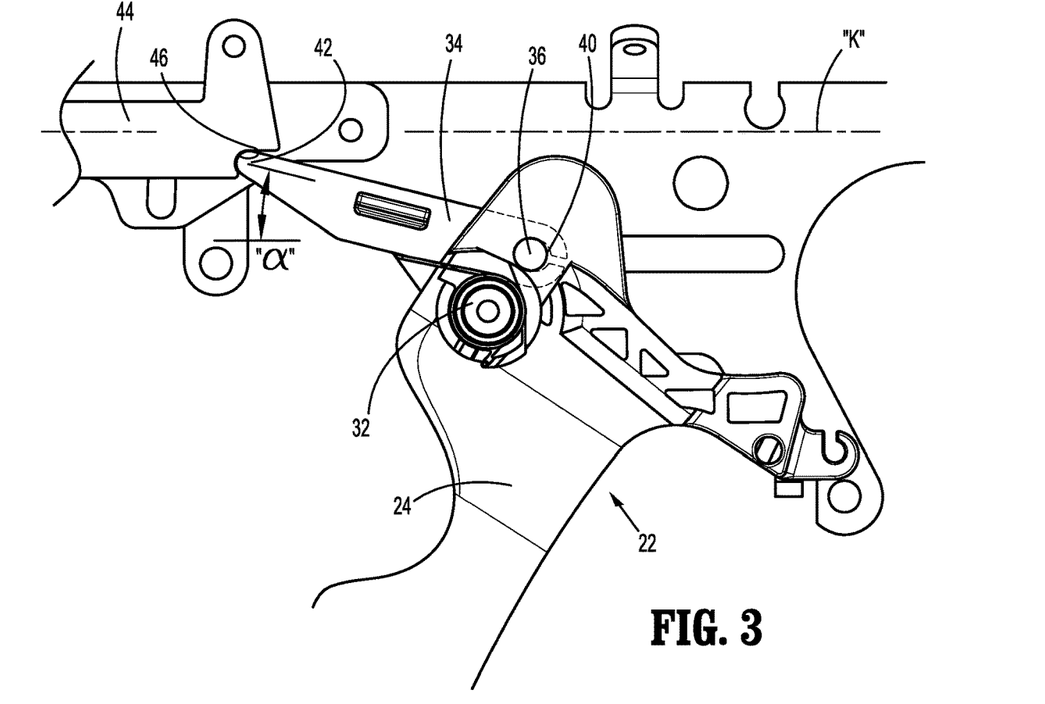
FIG. 3 is a side elevation view illustrating the thrust link of the trigger mechanism in engagement with the thrust member and the trigger in an initial position.

Referring to FIGS. 2-3, the trigger 24 is mounted to the handle frame 14 about pivot mount 32 which is coupled to the handle frame 14 through conventional methodologies. A thrust link 34 is coupled to the trigger 24 via reception of a thrust link pin 36 extending through openings 38 of the trigger 24 and received within an aperture 40 of the thrust link 34. The thrust link 34 defines a forward end 42 which is couplable to a thrust member 44 extending through the elongate member 18. In embodiments, the thrust member 44 may define a rear notch 46 which receives the forward end 42 of the thrust link 34 to couple the thrust link 34 with the thrust member 44. A torsion spring 48 is positioned about the pivot mount 32 of the trigger 24 to normally bias the thrust link 34 upwardly in position to couple with the thrust member 44. The thrust member 44 is configured for longitudinal movement to control operation of the end effector 20 upon actuation of the trigger 24 and movement of the thrust link 34.

Figure 4:
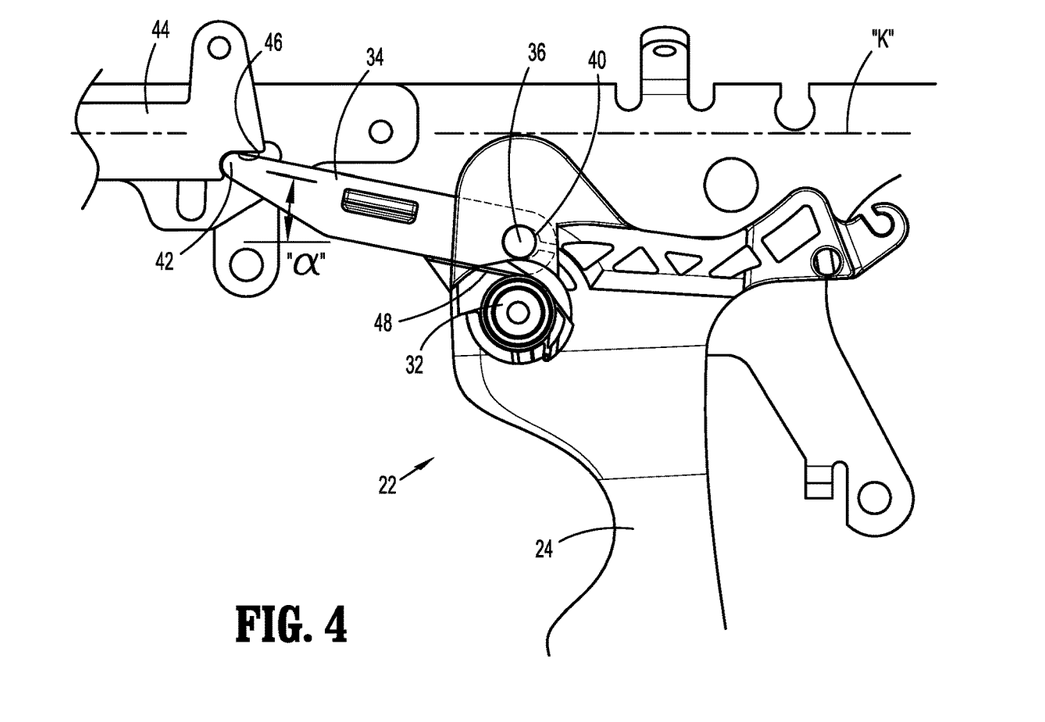
FIG. 4 is a side elevation view similar to the view of FIG. 3 with the trigger in an actuated position and the thrust link driving the thrust member to control operation of the end effector of the stapling instrument.
Figure 5:
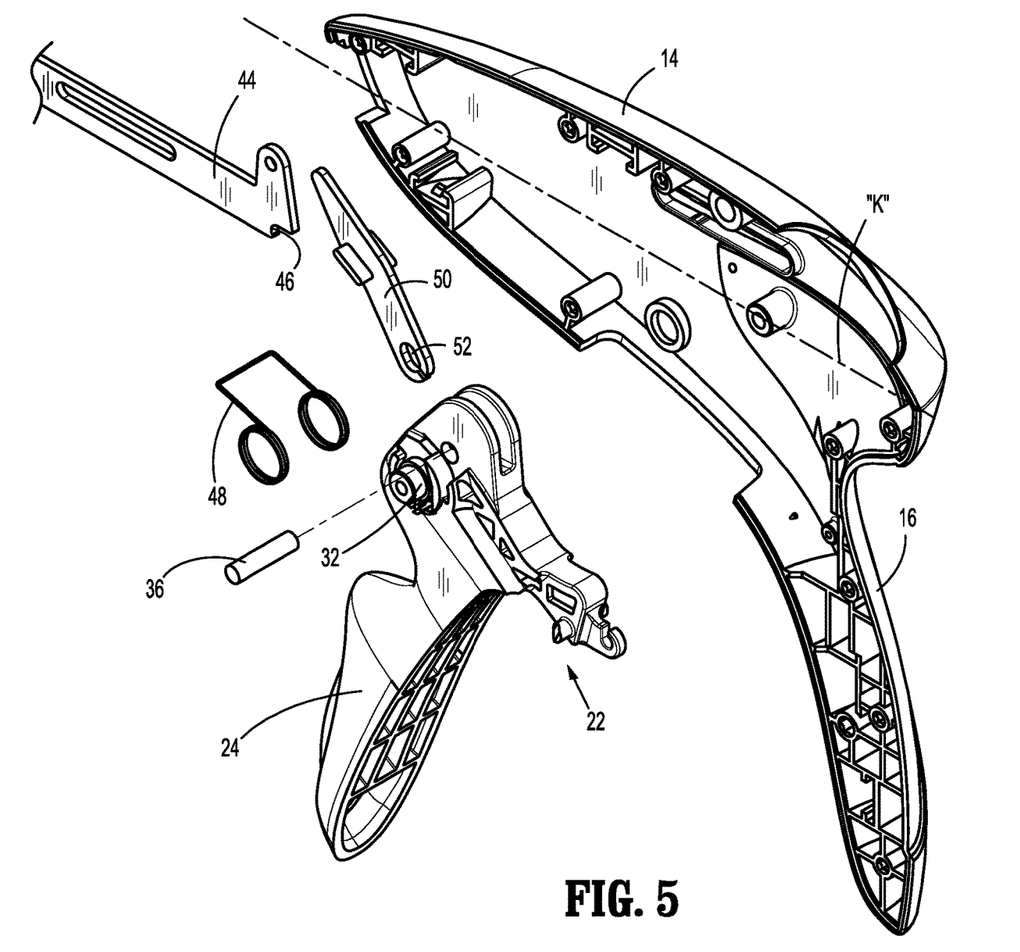
FIG. 5 is an exploded perspective view of the handle and trigger mechanism in accordance with another exemplary embodiment of the present disclosure.
Figure 6:
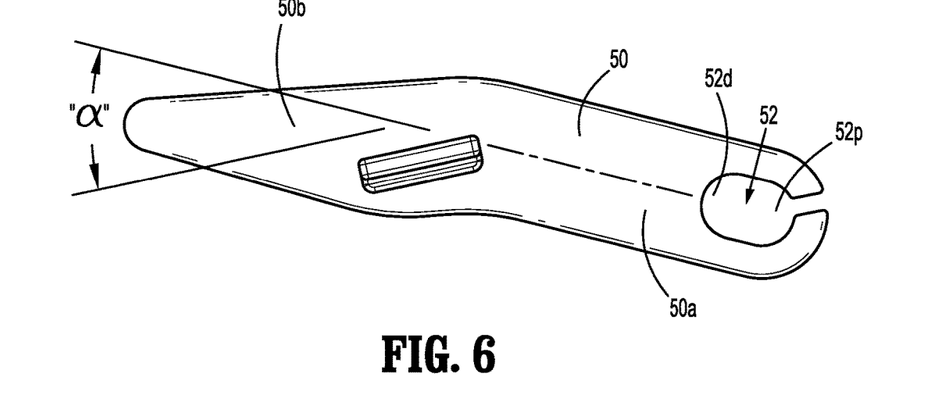
FIG. 6 is a side elevation view of the thrust link of the trigger mechanism of FIG. 5.
Figure 7:
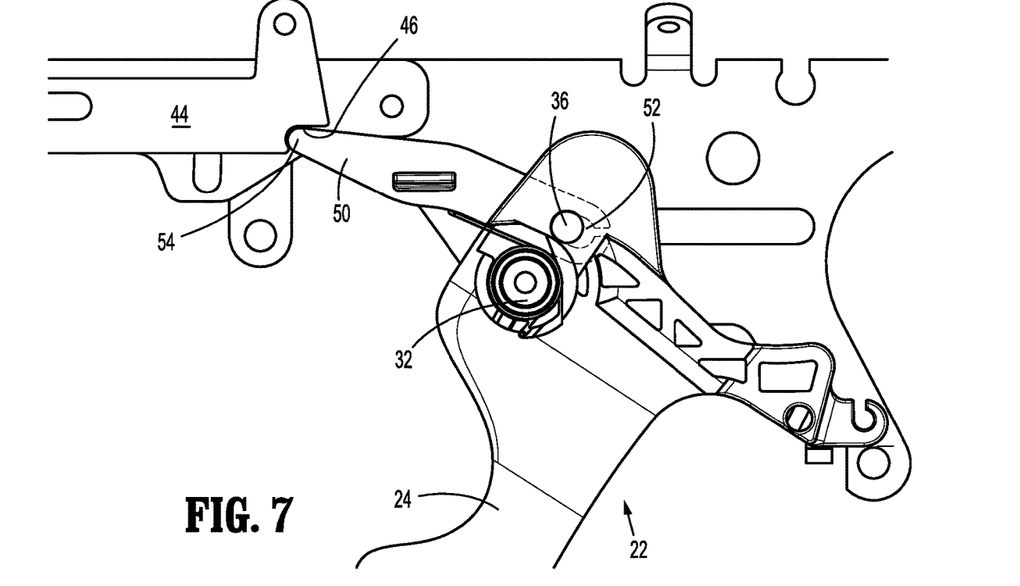
FIG. 7 is a side elevation view illustrating the thrust link of the trigger mechanism of FIG. 5 in engagement with the thrust member and the trigger in an initial position.
Figure 8:
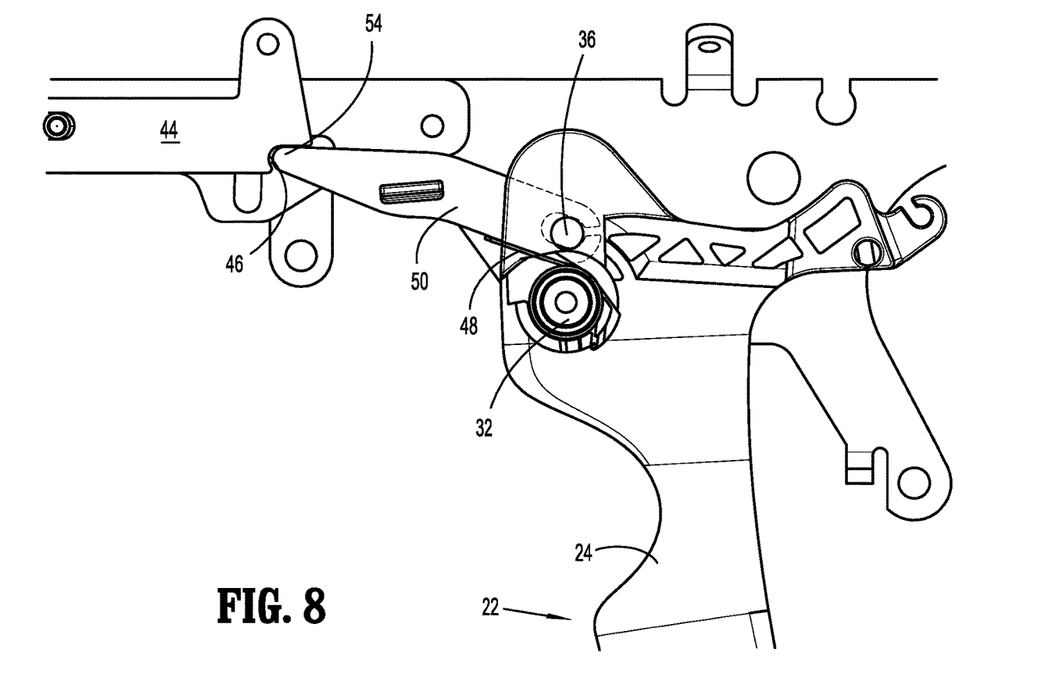
FIG. 8 is a side elevation view similar to the view of FIG. 7 with the trigger in an actuated position and the thrust link driving the thrust member to control operation of the end effector of the stapling instrument.

In embodiments, the thrust link 34, the torsion spring 48, and the thrust member 44 are cooperatively configured to maintain the thrust link 34 at a predetermined angle "α" with respect to the longitudinal handle axis "k" during movement of the thrust member 44 through a complete firing stroke. The angle "α" may range between about 1° to about 30° relative to the longitudinal handle axis "k". With this arrangement, the thrust link 34 does not pivot relative to the longitudinal handle axis "k", which, in effect, causes direct linear movement of the thrust link 34 and the thrust member 44 during pivoting movement of the trigger 24 from the initial position of FIG. 3 to the actuated position of FIG. 4. Otherwise stated, there is a direct linear relationship of the travel distance of the thrust link 34 and the thrust member 44 relative to the pivotal movement of the trigger 24. Consequently, the length of the firing stroke of the thrust member 44 is increased while the degree of pivotal movement of the trigger 24 required to effectuate the firing stroke to deploy the staples from the staple cartridge 28 and/or advance the knife is decreased thereby enhancing the mechanical advantage of the trigger mechanism 22 relative to conventional mechanisms.

Referring now to FIGS. 5-8, another exemplary embodiment of the trigger mechanism of the present disclosure is illustrated. This embodiment is substantially similar to the embodiment of FIGS. 1-4 and reference is made to the prior discussion for a description of like components. However, in accordance with this embodiment, the thrust link 50 defines an elongated slot 52, e.g., elongated along the longitudinal handle axis "k", which accommodates the thrust link pin 36. In the initial position of the trigger 24 depicted in FIG. 7, the thrust link pin 36 is positioned within the distal end 52d (FIG. 6) of the elongated link slot 52. Upon pivotal movement of the trigger 24 to the actuated position of FIG. 8, the thrust link 50 slightly pivots about the thrust bar link 36 to initially drive the thrust member 44. Continued pivotal movement of the trigger 24 causes the thrust link pin 36 to traverse the elongated slot 52 of the thrust link 50 and engage the proximal end 52p (FIG. 6) of the elongated slot 52 to move the thrust link 50 in a substantially linear manner. Thus, the length of the firing stroke of the thrust member 44 is increased while the degree of pivotal movement of the trigger 24 to the actuated position is minimized. In addition, the thrust link 50 includes a rear portion 50a and an offset forward portion 50b offset relative to the proximal portion 50a at an oblique angle "a" ranging from, e.g., between about 5° and 30°. (FIG. 6) This offset arrangement of the forward portion 50b coupled with the biasing effect of the torsion spring 48 ensures that the forward end 54 of the thrust link 50 remains engaged or received within the rear notch 46 of the thrust member 44 during movement of the trigger 24 from the initial position to the actuated position.

Figure 9:
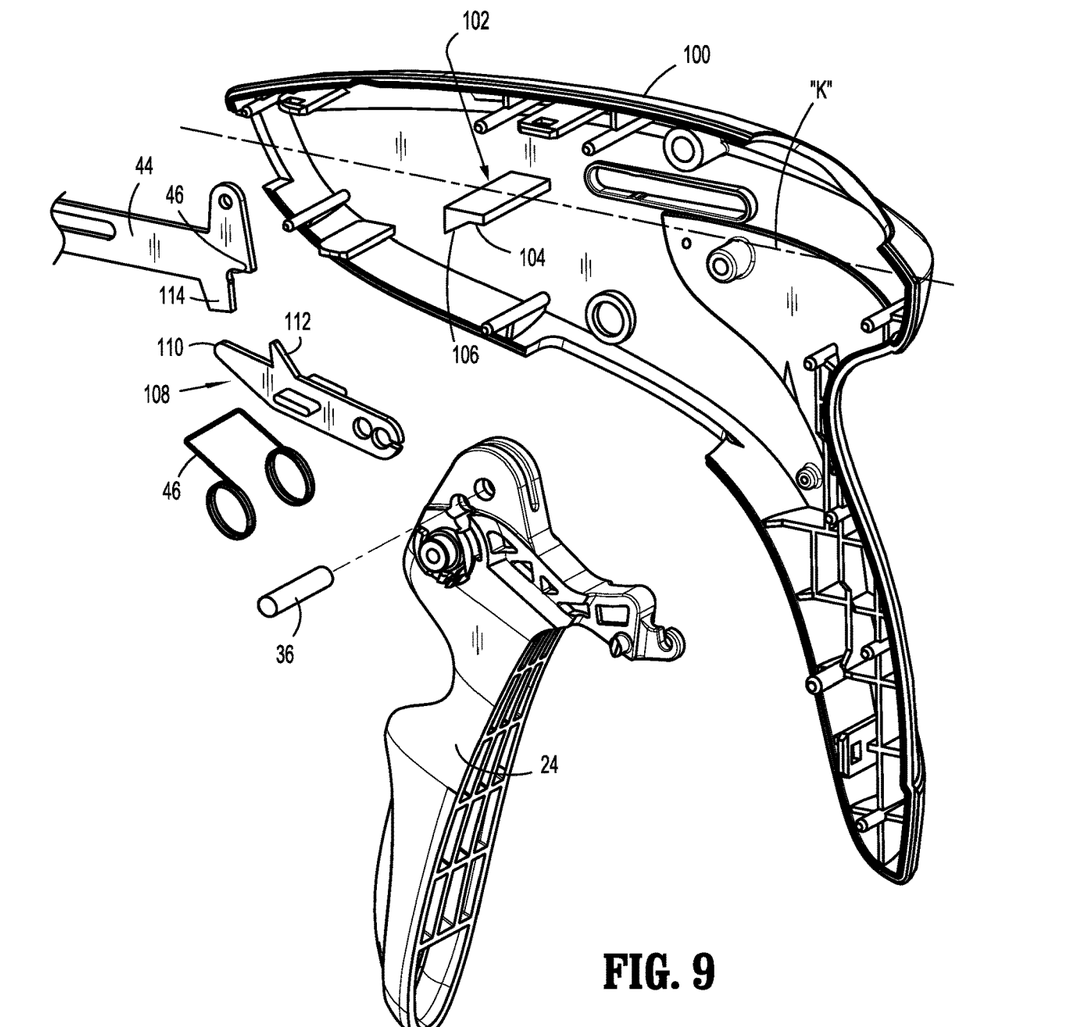
FIG. 9 is an exploded perspective view of the handle and trigger mechanism in accordance with another exemplary embodiment of the present disclosure.
Figure 10:
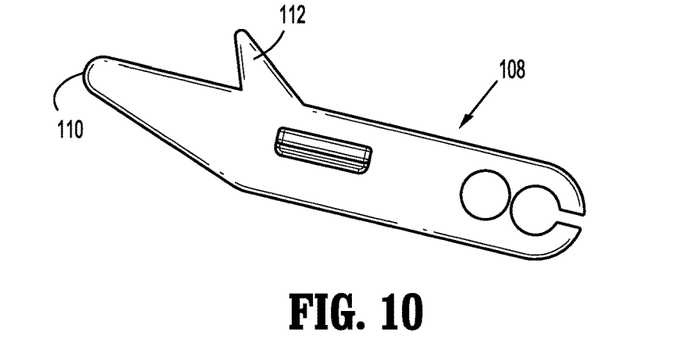
FIG. 10 is a side elevation view of the thrust link of the trigger mechanism of FIG. 9.
Figure 11:
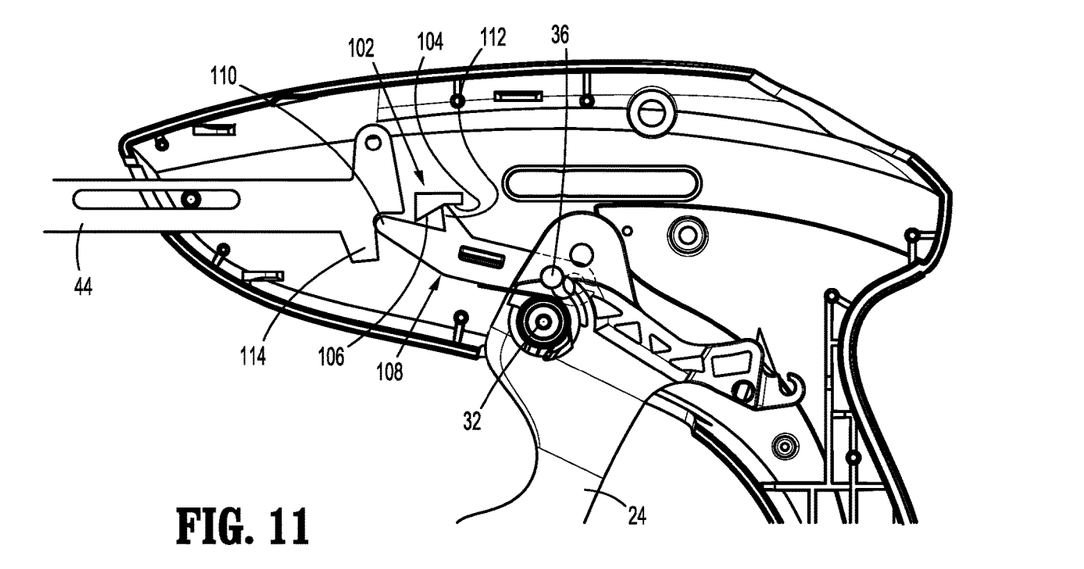
FIG. 11 is a side elevation view illustrating the thrust link of the trigger mechanism of FIG. 9 in engagement with the thrust member and the trigger in an initial position.

Referring now to FIGS. 9-11, another exemplary embodiment of the trigger mechanism of the present disclosure is illustrated. This embodiment is substantially similar to the embodiment of FIGS. 5-8 and reference is made to the prior discussion for a description of like components. However, in accordance with this embodiment, the handle frame 100 includes an internal guide member 102 disposed about midway through the handle frame 100. The guide member 102 has a horizontal surface component 104 in general parallel relation with the longitudinal handle axis "k" and an angled surface component 106 in oblique relation to the longitudinal axis "k". A thrust link 108 is coupled to the trigger 24 and has a forward drive cam 110 and a guide cam 112 depending outwardly from an intermediate segment of the thrust link 108. The forward drive cam 110 couples with the thrust member 44. The guide cam 112 is engageable with the guide member 102, specifically, the horizontal surface and angled surface components 104, 106 of the guide member 102 during pivotal movement of the trigger 24.

Figure 12:
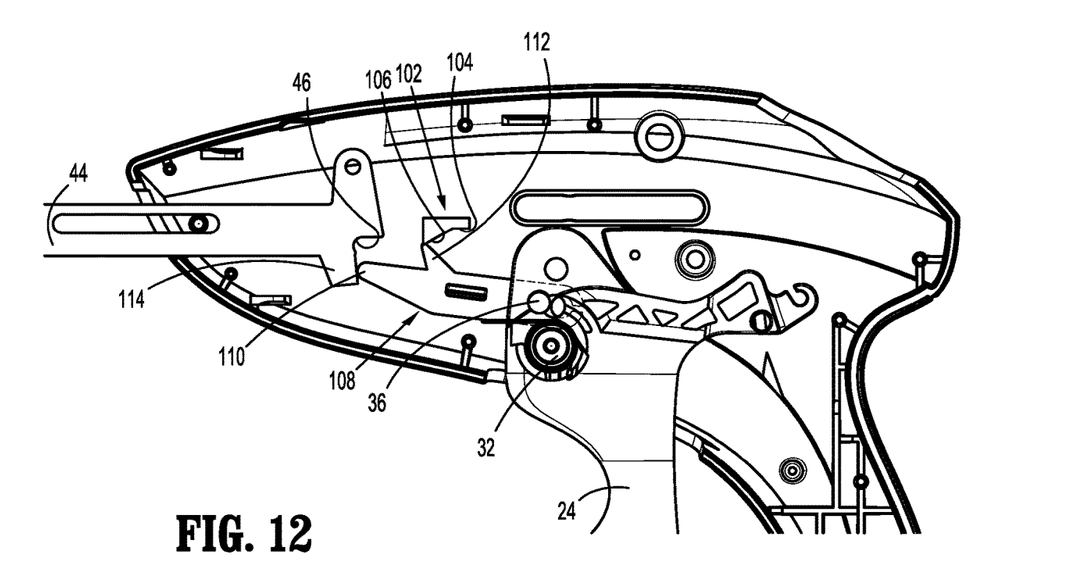
FIG. 12 is a side elevation view similar to the view of FIG. 11 with the trigger in a partial actuated position during a first stage of longitudinal movement of the thrust member.
Figure 13:
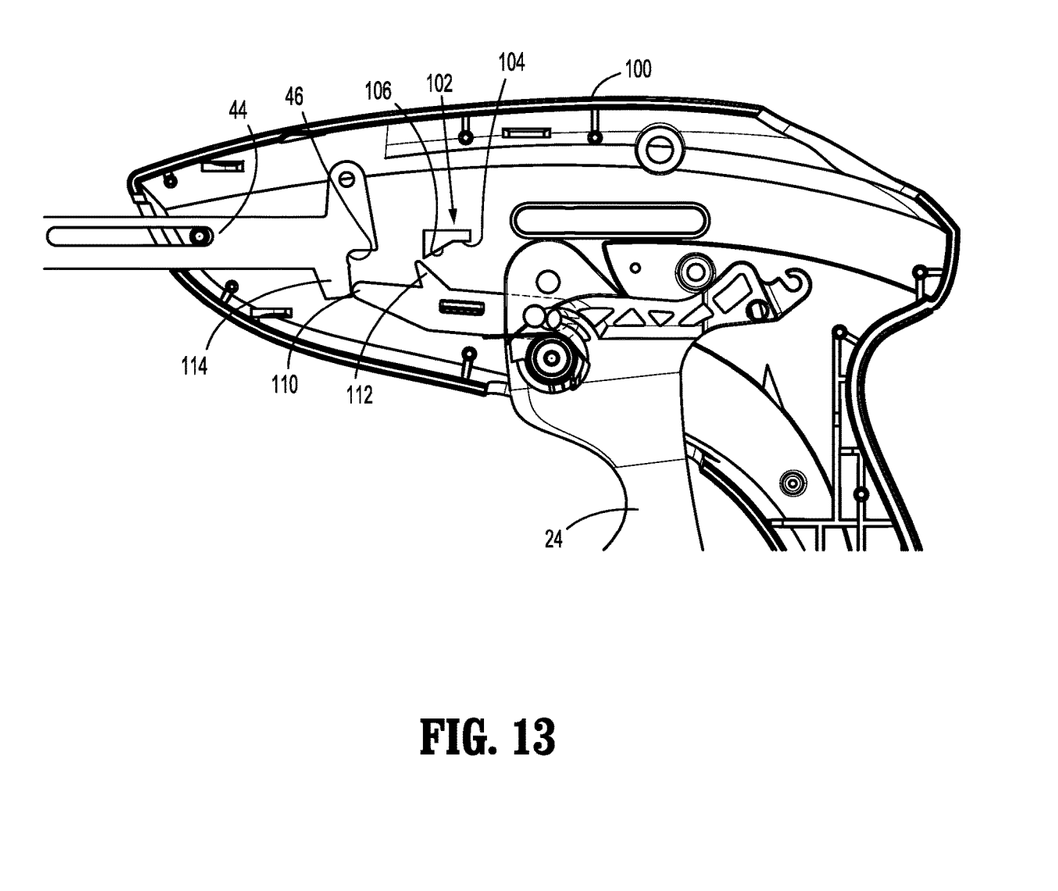
FIG. 13 is a side elevation view similar to the view of FIG. 12 with the trigger in a fully actuated position and the thrust link driving the thrust member through a second stage of longitudinal movement to control operation of the end effector of the stapling instrument.

The thrust member 44 includes rear notch 46 and a thrust bar arm 114 depending downwardly from the rear notch 46. In the initial position of the trigger 24 depicted in FIG. 11, the forward drive cam 110 of the thrust link 108 is at least partially accommodated within the rear notch 46 of the thrust member 44 and the guide cam 112 is in engagement with the guide member 102, e.g., adjacent the intersection of the horizontal surface component 104 and the angled surface component 106. Upon movement of the trigger 24 to the partial actuated position of FIG. 12, the guide cam 112 traverses the angled surface component 106 of the guide member 102 causing the thrust link 108 to pivot about the thrust link pin 36 and also cause the forward drive cam 110 of the thrust link 108 to traverse the thrust bar arm 114 of the thrust member 44 thereby advancing the thrust member 44 through a first stage of longitudinal movement. Upon movement of the trigger 24 to the fully actuated position of FIG. 13, the guide cam 112 is released from the guide member 102 such that pivotal movement of the thrust link 108 about the thrust link pin 36 is discontinued, and the thrust link 108 is advanced in a linear manner to drive the thrust bar arm 114 and the thrust member 44 corresponding to a second stage of longitudinal movement of the thrust member 44. The extended characteristic of the thrust bar arm 114 provides an increased length of the firing stroke (i.e., including the first and second stages of longitudinal movement of the thrust member 44) for the same angular rotation of the trigger 24 to further advance the thrust member 44 and effect operation of the end effector 20.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical instrument, comprising:
   a handle including a handle frame defining a longitudinal handle axis and having an internal guide member with an internal guide surface;
   an elongate member extending from the handle frame;
   an end effector coupled to the elongate member;
   a thrust member extending through the elongate member and coupled to the end effector, the thrust member configured for longitudinal movement to control operation of the end effector, the thrust member defining a thrust bar arm; and
   a trigger mechanism, including:
      a trigger pivotally mounted to the handle frame and configured for movement between an initial position and an actuated position; and
      a thrust link coupled to the trigger, the thrust link having a forward drive cam engageable with the thrust bar arm of the thrust member and a guide cam engageable with the internal guide surface of the guide member of the handle frame, the thrust link configured to pivot upon movement of the trigger from the initial position to the actuated position through traversing movement of the guide cam along the internal guide surface of the guide member to cause corresponding traversing movement of the forward drive cam of the thrust link along the thrust bar arm of the thrust member to cause advancing movement of the thrust member through at least a first stage of longitudinal movement to operate the end effector.

2. The surgical instrument according to claim 1 wherein the internal guide surface of the internal guide member is arranged in oblique relation to the longitudinal handle axis.

3. The surgical instrument according to claim 2 wherein the trigger is operable between the initial position, the actuated position and a partial actuated position intermediate the initial and actuated positions.

4. The surgical instrument according to claim 3 wherein the guide member of the handle frame is configured such that the internal guide surface is released relative to the guide cam of the thrust link upon movement of the trigger beyond the partial actuated position whereby continued movement of the trigger to the actuated position drives the thrust link in a linear manner.

\* \* \* \* \*